(12) United States Patent
Schneider et al.

(10) Patent No.: US 8,796,496 B2
(45) Date of Patent: *Aug. 5, 2014

(54) PROCESS FOR PREPARING BENZENE FROM METHANE

(75) Inventors: Christian Schneider, Mannheim (DE); Martin Karches, Neustadt (DE); Joana Coelho Tsou, Heidelberg (DE); Sebastian Ahrens, Wiesloch (DE); Dieter Stuetzer, Dudenhofen (DE)

(73) Assignee: BASF SE, Ludwigshafen (DE)

( * ) Notice: Subject to any disclaimer, the term of this patent is extended or adjusted under 35 U.S.C. 154(b) by 70 days.

This patent is subject to a terminal disclaimer.

(21) Appl. No.: 13/393,837

(22) PCT Filed: Aug. 23, 2010

(86) PCT No.: PCT/EP2010/062213
§ 371 (c)(1),
(2), (4) Date: Mar. 2, 2012

(87) PCT Pub. No.: WO2011/026744
PCT Pub. Date: Mar. 10, 2011

(65) Prior Publication Data
US 2012/0165585 A1    Jun. 28, 2012

(30) Foreign Application Priority Data
Sep. 3, 2009 (EP) ..................... 09169359

(51) Int. Cl.
*C07C 2/76* (2006.01)
*C07C 15/02* (2006.01)

(52) U.S. Cl.
USPC ............ 585/415; 585/410; 585/904; 585/906

(58) Field of Classification Search
CPC .................................. C07C 2/76; C07C 15/02
USPC .................................. 585/415, 410, 904, 906
See application file for complete search history.

(56) References Cited

U.S. PATENT DOCUMENTS

| 2,367,281 A * | 1/1945 | Johnson .................. 208/119 |
| 5,049,361 A | 9/1991 | Harandi et al. |
| 2003/0083535 A1 | 5/2003 | Wright et al. |
| 2007/0249879 A1 | 10/2007 | Iaccino et al. |
| 2007/0249880 A1 | 10/2007 | Iaccino et al. |
| 2008/0249342 A1 * | 10/2008 | Iaccino et al. ............ 585/402 |
| 2011/0060176 A1 | 3/2011 | Kiesslich et al. |
| 2011/0124933 A1 | 5/2011 | Kiesslich et al. |
| 2011/0130606 A1 | 6/2011 | Kiesslich et al. |
| 2011/0303550 A1 | 12/2011 | Coelho Tsou et al. |
| 2012/0012467 A1 | 1/2012 | Coelho Tsou et al. |
| 2012/0012471 A1 | 1/2012 | Coelho Tsou et al. |
| 2012/0022310 A1 | 1/2012 | Schneider et al. |

FOREIGN PATENT DOCUMENTS

| JP | 2003-26613 A | 1/2003 |
| JP | 2005-343879 A | 12/2005 |
| WO | 03 000826 | 1/2003 |
| WO | 2009 124902 | 10/2009 |

OTHER PUBLICATIONS

U.S. Appl. No. 13/479,961, filed May 24, 2012, Stroefer, et al.
Kunii, D., et al., "Fluidization Engineering," Second Edition, pp. 211-215 and 237-243, (1923).
"Handbook of Fluidization and Fluid-Particle Systems," Chapter 7, pp. 194-195, (2003).
International Search Report Issued Apr. 5, 2011 in PCT/EP10/62213 Filed Aug. 23, 2010.
Office Action issued Aug. 26, 2013 in Japanese Patent Application No. 2012-527278 (submitting English translation only).

* cited by examiner

*Primary Examiner* — Thuan D Dang
(74) *Attorney, Agent, or Firm* — Oblon, Spivak, McClelland, Maier & Neustadt, L.L.P.

(57) ABSTRACT

The present invention relates to a process for nonoxidatively dehydroaromatizing a reactant stream comprising $C_1$-$C_4$-aliphatics, comprising the steps of I. feeding reactant stream E into a reaction zone 1, converting reactant stream E under nonoxidative conditions in the presence of a particulate catalyst to a product stream P comprising aromatic hydrocarbons and discharging product stream P from reaction zone 1, II. transferring the catalyst with reduced activity as a result of deposited coke into a reaction zone 2, III. at least partly regenerating the catalyst with supply of a hydrogen-comprising gas stream H in a reaction zone 2, at least some of the coke deposited being converted to methane to form a methane-comprising gas stream M which is fed at least partly to reaction zone 1, IV. discharging the catalyst from reaction zone 2 and V. recycling at least a portion of the discharged catalyst into reaction zone 1, reaction zone 1 and reaction zone 2 being arranged spatially adjacent to one another in the same reactor.

19 Claims, 1 Drawing Sheet

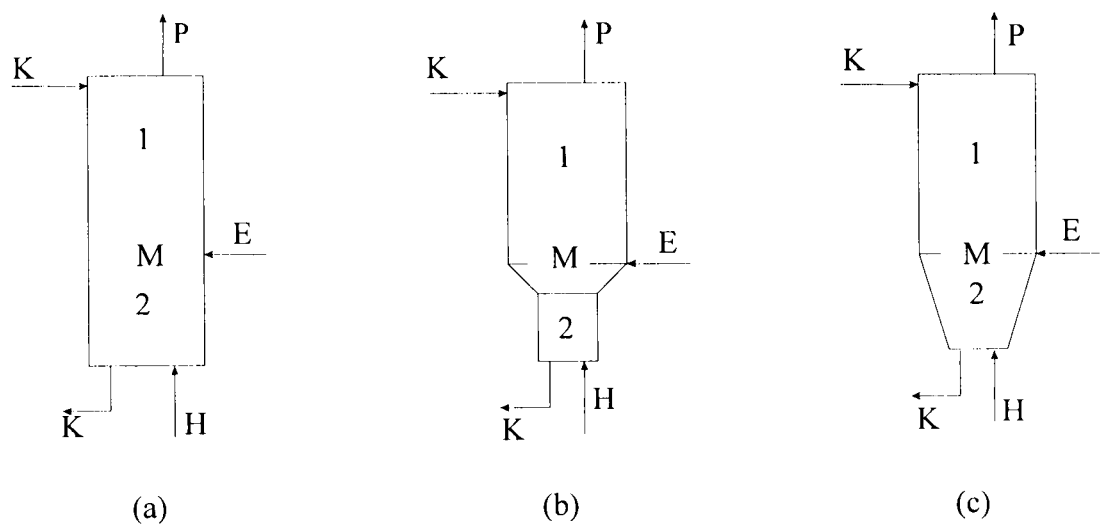

PROCESS FOR PREPARING BENZENE FROM METHANE

CROSS REFERENCE TO RELATED APPLICATION

This application is a National Stage entry under 35 USC 371 of PCT/EP 10/062213, filed on Aug. 23, 2010, and claims priority to European Patent Application No. 09169359.8, filed on Sep. 3, 2009.

The present invention relates to a process for nonoxidatively dehydroaromatizing a reactant stream comprising $C_1$-$C_4$-aliphatics by converting the reactant stream in the presence of a catalyst in a reaction zone 1 to a product stream P comprising aromatic hydrocarbons, and regenerating the catalyst with reduced activity as a result of deposited coke with a hydrogen-comprising mixture H in a reaction zone 2, withdrawing the catalyst from reaction zone 2 and recycling the catalyst into reaction zone 1.

Aromatic hydrocarbons such as benzene, toluene, ethylbenzene, styrene, xylene and naphthalene are important intermediates in the chemical industry, the demand for which continues to rise. In general, they are obtained by catalytic reformation from naphtha which is in turn obtained from mineral oil. Recent studies show that global mineral oil reserves are more limited compared with natural gas reserves. Therefore, the preparation of aromatic hydrocarbons from reactants which can be obtained from natural gas has become another alternative of economic interest. The main component of natural gas is typically methane.

One possible reaction route for obtaining aromatics from aliphatics is nonoxidative dehydroaromatization (DHAM). This reaction is effected under nonoxidative conditions, more particularly with exclusion of oxygen. In DHAM, dehydrogenation and cyclization of the aliphatics take place to give the corresponding aromatics with release of hydrogen.

A great problem for the industrial application of dehydroaromatization under nonoxidative conditions is that of coking, since it lowers the activity of the catalyst within a relatively short time, which leads to short production cycles and a high regeneration requirement. Moreover, coking is frequently accompanied by a shortened lifetime of the catalyst. Regeneration of the catalysts is not unproblematic, since the starting activities firstly have to be regularly re-establishable for an economically viable process and this secondly has to be possible over a large number of cycles.

Moreover, the coke deposits have an unfavorable effect on the mass balance and the yield, since every molecule of reactant which is converted to coke is no longer available for the desired reaction to give aromatics. The coke selectivities achieved to date in the prior art are in most cases more than 20% based on the aliphatic converted.

A further difficulty in the industrial performance of DHAM lies in the introduction of the heat of reaction required. DHAM is an endothermic reaction which is reliant on external heat supply. When the reaction is heated indirectly, large heat exchange surfaces are required, which make the process complicated in apparatus terms and costly in economic terms. Furthermore, undesired side reactions take place on the heat exchange surfaces owing to the relatively high temperatures, for example coking.

WO-A 03/000826 describes a process for aromatizing methane, in which the methane is converted in a reaction zone in the presence of an active catalyst, in the course of which the catalyst is deactivated. A portion of the deactivated catalyst is regenerated with a regenerating gas in a regeneration zone, the catalyst circulating between the reaction zone and the regeneration zone. The regenerating gases used may be oxygen or air, hydrogen and steam. The gases formed in the regeneration are not used any further. The heat arising in the regeneration is transferred into the reaction zone through the catalyst itself or else other heat exchange media.

US-A 2007/0249879 relates to a process for converting methane to higher hydrocarbons including aromatics. The reactor used consists of at least two series-connected reaction zones. The catalyst which is present in particulate form is conducted from the first into the second reaction zone, the methane-containing stream in the reverse direction from the second into the first reaction zone. A conversion of the methane to product takes place in all reaction zones. Portions of the catalyst can be withdrawn for regeneration and returned after the regeneration. The regeneration is effected by means of an oxygenous gas. If appropriate, the catalyst is subsequently activated with a hydrogenous gas. To supply heat to the reaction system, a portion of the catalyst can be withdrawn and heated up in a separate heating zone with combustion gases which stem from an additional fuel source. The heated catalyst is then returned to the reaction zone.

US-A 2007/0249880 discloses a process for converting methane to aromatic hydrocarbons in the presence of a catalyst, the reaction zone being run with an inverse temperature profile. Here too, the catalyst can be regenerated after withdrawal and/or heated to temperatures above the reaction temperature by means of combustion gases, and then returned to the reaction zones in each case.

In the processes known from the prior art, the catalyst particles, as a result of the many necessary transfer operations between reaction zone, regeneration zone and heating zone, are exposed to significant mechanical stresses which lead to a shortening of the lifetime of the catalysts. Moreover, material utilization, i.e. conversion to desired product of the offgases obtained in the course of regeneration of the catalyst, is not at all in the case of oxidative regeneration or associated with a certain level of technical complexity in the case of regeneration with hydrogen.

Over and above the processes known in the prior art, there is a need for further, improved processes for preparing aromatics from $C_1$-$C_4$-aliphatics, which have a high yield of aromatic hydrocarbons in relation to the $C_1$-$C_4$-aliphatics used and in which the catalyst is exposed to lower mechanical stresses.

This object is achieved in accordance with the invention by a process for nonoxidatively dehydroaromatizing a reactant stream E comprising $C_1$-$C_4$-aliphatics, comprising the steps of I. feeding reactant stream E into a reaction zone 1, converting reactant stream E under nonoxidative conditions in the presence of a particulate catalyst to a product stream P comprising aromatic hydrocarbons and discharging product stream P from reaction zone 1, II. transferring the catalyst with reduced activity as a result of deposited coke into a reaction zone 2, III. at least partly regenerating the catalyst with supply of a hydrogen-comprising gas stream H in a reaction zone 2, at least some of the coke deposited being converted to methane to form a methane-comprising gas stream M which is fed at least partly to reaction zone 1, IV. discharging at least a portion of the catalyst from reaction zone 2 and V. recycling at least a portion of the discharged catalyst into reaction zone 1, reaction zone 1 and reaction zone 2 being arranged spatially adjacent to one another in the same reactor.

When the deactivated catalyst is regenerated with hydrogen, methane forms from the coke deposits in an exothermic reaction. According to the invention, this methane is fed at least partly to reaction zone 1 and is thus available again as a reactant. This leads to an increase in the overall yield of aromatics based on the amount of $C_1$-$C_4$-aliphatics used.

The spatially adjacent arrangement of reaction zone 1 in which the DHAM is performed and of the regeneration zone (reaction zone 2) dispenses with transport pathways and reduces the mechanical stress resulting from the transfer of the catalyst particles. The heat generated in the course of regeneration of the catalyst is transferred directly into reaction zone 1 by the recycling of at least a portion of the catalyst and of gas stream M. This generates a portion of the heat of reaction required for the aromatization in the system itself, which is a technically particularly simple means of supplying energy. Overall, the inventive zoning of the reactor or reaction bed in at least one aromatization zone (reaction zone 1) and an adjoining regeneration zone (reaction zone 2) enables better exploitation of the mass and heat flows with lower mechanical stress on the catalyst used.

According to the present invention, "nonoxidative" means, in relation to the DHAM, that the concentration of oxidizing agents such as oxygen or nitrogen oxides in reactant stream E is below 5% by weight, preferably below 1% by weight, more preferably below 0.1% by weight. Most preferably, the mixture is free of oxygen. Likewise particularly preferred is a concentration of oxidizing agents in the mixture E which is equal to or less than the concentration of oxidizing agents in the source from which the $C_1$-$C_4$-aliphatics originate.

In relation to the regeneration, "nonoxidative" in the context of the present invention means that the coke deposits originating from the DHAM on the catalyst, to regenerate the catalyst, are not converted to CO and/or $CO_2$ by means of oxidizing agents such as air or oxygen. In particular, the concentration of oxidizing agents in the mixture H for use for regeneration in step III is below 5% by weight, preferably below 1% by weight, more preferably below 0.1% by weight.

According to the invention, reactant stream E comprises at least one aliphatic having 1 to 4 carbon atoms. These aliphatics include, for example, methane, ethane, propane, n-butane, isobutane, ethene, propene, 1- and 2-butene, isobutene. In one embodiment of the invention, reactant stream E comprises at least 50 mol %, preferably at least 60 mol %, more preferably at least 70 mol %, exceptionally preferably at least 80 mol %, especially at least 90 mol %, of $C_1$-$C_4$-aliphatics.

Among the aliphatics, particular preference is given to using the saturated alkanes; in that case, reactant stream E comprises preferably at least 50 mol %, preferably at least 60 mol %, more preferably at least 70 mol %, exceptionally preferably at least 80 mol %, especially at least 90 mol %, of alkanes having 1 to 4 carbon atoms.

Among the alkanes, methane and ethane are preferred, especially methane. In this embodiment of the present invention, reactant stream E comprises preferably at least 50 mol %, preferably at least 60 mol %, more preferably at least 70 mol %, exceptionally preferably at least 80 mol %, especially at least 90 mol %, of methane.

The source used for the $C_1$-$C_4$-aliphatics is preferably natural gas. The typical composition of natural gas is as follows: 75 to 99 mol % of methane, 0.01 to 15 mol % of ethane, 0.01 to 10 mol % of propane, up to 6 mol % of butane, up to 30 mol % of carbon dioxide, up to 30 mol % of hydrogen sulfide, up to 15 mol % of nitrogen and up to 5 mol % of helium. Before use in the process according to the invention, the natural gas can be purified and enriched by methods known to those skilled in the art. The purification includes, for example, the removal of any hydrogen sulfide or carbon dioxide present in the natural gas and of further compounds which are undesired in the subsequent process.

The $C_1$-$C_4$-aliphatics present in reactant stream E may also stem from other sources, for example may have originated in the course of crude oil refining. The $C_1$-$C_4$-aliphatics may also have been produced by renewable means (e.g. biogas) or synthetic means (e.g. Fischer-Tropsch synthesis).

If the $C_1$-$C_4$-aliphatic source used is biogas, reactant stream E may additionally also comprise ammonia, traces of lower alcohols and further additives typical of biogas.

In a further embodiment of the process according to the invention, the reactant stream E used may be LPG (liquid petroleum gas). In a further embodiment of the process according to the invention, the reactant stream E used may be LNG (liquefied natural gas).

It is additionally possible to add hydrogen, steam, carbon monoxide, carbon dioxide, nitrogen and one or more noble gases to reactant stream E. Reactant stream E preferably comprises hydrogen, preferably 0.1 to 10% by volume of hydrogen, more preferably 0.1 to 5% by volume of hydrogen.

In step I of the process according to the invention, reactant stream E is fed to a reaction zone 1. In reaction zone 1, reactant stream E is converted under nonoxidative conditions in the presence of a particulate catalyst to a product stream P comprising aromatic hydrocarbons. This conversion is a dehydroaromatization, i.e. the $C_1$-$C_4$-aliphatics present in reactant stream E react with dehydrogenation and cyclization to give the corresponding aromatics, which releases hydrogen. According to the invention, the DHAM is performed in the presence of suitable catalysts. Generally, all catalysts which catalyze DHAM can be used in step I of the process according to the invention. The person skilled in the art is aware of such catalysts, and also processes for preparation thereof. Typically, the DHAM catalysts comprise a porous support and at least one metal applied thereto. The supports used are typically a crystalline or amorphous inorganic compound.

According to the invention, the catalyst preferably comprises at least one metalosilicate as a support. Preference is given to using aluminum silicates as supports. Very particular preference is given in accordance with the invention to using zeolites as supports. Preferably in accordance with the invention, the zeolite present in the catalysts has a structure selected from the pentasil and MWW structure types and more preferably from the MFI, MEL, mixed MFI/MEL and MWW structure types. Very particular preference is given to using a zeolite of the ZSM-5 or MCM-22 type. The designations of the structure types of the zeolites correspond to the information in W. M. Meier, D. H. Olson and Ch. Baerlocher, "Atlas of Zeolite Structure Types", Elsevier, 3rd edition, Amsterdam 2001. The synthesis of the zeolites is known to those skilled in the art and can, for example, be carried out proceeding from alkali metal aluminate, alkali metal silicate and amorphous $SiO_2$ under hydrothermal conditions. In this synthesis, the type of channel systems formed in the zeolite can be controlled by means of organic template molecules, by means of the temperature and further experimental parameters.

In addition to Al, the zeolites may comprise further elements such as Ga, B, Fe or In.

Typically, the DHAM catalyst comprises at least one metal. Typically, the metal is selected from groups 3 to 12 of the Periodic Table of the Elements (IUPAC). Preferably in accordance with the invention, the DHAM catalyst comprises at least one element selected from the transition metals of main groups 6 to 11. The DHAM catalyst more preferably comprises Mo, W, Mn, Tc, Re, Fe, Ru, Os, Co, Rh, Ir, Ni, Pd, Pt, Cu, Ag, Au. More particularly, the DHAM catalyst comprises at least one element selected from the group of Mo, W, Re, Fe, Ru, Os, Co, Rh, Ir, Ni, Pd, Pt, Cu. Most preferably, the DHAM catalyst comprises at least one element selected from the group of Mo, W and Re.

Likewise preferably in accordance with the invention, the DHAM catalyst comprises at least one metal as an active component and at least one further metal as a dopant. According to the invention, the active component is selected from Mo, W, Re, Ru, Os, Rh, Ir, Pd, Pt. According to the invention, the dopant is selected from the group of Cr, Mn, Fe, Co, Ni, Cu, V, Zn, Zr and Ga, preferably from the group of Fe, Co, Ni, Cu. According to the invention, the DHAM catalyst may comprise more than one metal as an active component and more than one metal as a dopant. These are each selected from the metals specified for the active component and the dopant.

According to the invention, the at least one metal is applied to the support by wet chemical or dry chemical methods known to those skilled in the art.

According to the invention, the catalyst comprises 0.1 to 20% by weight, preferably 0.2 to 15% by weight, more preferably 0.5 to 10% by weight, based in each case on the total weight of the catalyst, of the at least one metal.

According to the invention, the catalyst may comprise at least one metal from the group of the active components in conjunction with at least one metal selected from the group of the dopants. In this case, the concentration of the active component is 0.1 to 20% by weight, preferably 0.2 to 15% by weight, more preferably 0.5 to 10% by weight, based in each case on the total weight of the catalyst.

In this case, the dopant is present in the catalyst, according to the invention, in a concentration of at least 0.1% by weight, preferably at least 0.2% by weight, most preferably at least 0.5% by weight, based on the total weight of the catalyst.

In a further preferred embodiment of the present invention, the catalyst is mixed with a binder. Suitable binders are the customary binders known to those skilled in the art, such as aluminum oxide- and/or Si-containing binders. Particular preference is given to Si-containing binders; especially suitable are tetraalkoxysilanes, polysiloxanes and colloidal $SiO_2$ sols.

When the inventive catalyst comprises a binder, it is present in a concentration of from 5 to 80% by weight, based on the total weight of the catalyst, preferably from 10 to 50% by weight, more preferably from 10 to 30% by weight.

According to the invention, addition of the binder is followed by a shaping step, in which the catalyst material is processed by processes known to those skilled in the art to shaped bodies. Examples of shaping processes include spraying of a suspension comprising the support and/or the catalyst material, spray-drying, tableting, pressing in the moist or dry state and extrusion. Two or more of these processes may also be combined. For the shaping, it is possible to add assistants such as pore formers and pasting agents, or else other additives known to those skilled in the art.

Pore formers and/or pasting agents are, after the shaping, preferably removed from the resulting shaped body by at least one suitable drying and/or calcination step. The conditions required for this purpose can be selected analogously to the parameters described above for calcination and are known to those skilled in the art.

The geometry of the catalysts obtainable in accordance with the invention may, for example, be spherical (hollow or solid), cylindrical (hollow or solid), annular, saddle-shaped, star-shaped, honeycomb-shaped or tablet-shaped. In addition, extrudates are useful, for example in strand form, trilobal form, quatrolobal form, star form or hollow cylindrical form. In addition, the catalyst material to be shaped can be extruded and calcined, and the extrudates thus obtained can be crushed and processed to spall or powder. The spall can be separated into different screen fractions. In a preferred embodiment of the invention, the catalyst is used in the form of spray-dried particles, preferably spray powder. The particles are preferably round particles. The catalyst particles preferably have a size of 20 to 100 micrometers.

Preference is given to using catalyst geometries as known from the FCC (fuel catalytic cracking) process.

It may be advantageous to activate the catalyst used for dehydroaromatization of $C_1$-$C_4$-aliphatics before the actual reaction.

This activation can be effected with a $C_1$-$C_4$-alkane, for example ethane, propane, butane or a mixture thereof, preferably butane. The activation is carried out at a temperature of 250 to 850° C., preferably at 350 to 650° C., and a pressure of 0.5 to 5 bar, preferably at 0.5 to 2 bar. Typically, the GHSV (gas hourly space velocity) in the activation is 100 to 4000 $h^{-1}$, preferably 500 to 2000 $h^{-1}$.

However, it is also possible to carry out an activation by virtue of reactant stream E already comprising the $C_1$-$C_4$-alkane, or a mixture thereof, per se, or by adding the $C_1$-$C_4$-alkane, or a mixture thereof, to reactant stream E. The activation is carried out at a temperature of 250 to 650° C., preferably at 350 to 550° C., and a pressure of 0.5 to 5 bar, preferably at 0.5 to 2 bar.

In a further embodiment, it is also possible additionally to add hydrogen to the $C_1$-$C_4$-alkane.

In a preferred embodiment of the present invention, the catalyst is activated with an $H_2$-comprising gas stream which may additionally comprise inert gases such as $N_2$, He, Ne and Ar.

According to the invention, the dehydroaromatization of $C_1$-$C_4$-aliphatics is performed in the presence of a catalyst at temperatures of 400 to 1000° C., preferably of 500 to 900° C., more preferably of 600 to 800° C., especially of 700 to 800° C., at a pressure of 0.5 to 100 bar, preferably 1 to 30 bar, more preferably 1 to 10 bar, especially 1 to 5 bar. According to the present invention, the reaction is performed at a GHSV (gas hourly space velocity, volume of reactant flow/volume of the catalyst bed) of 10 to 10 000 $h^{-1}$, preferably 200 to 3000 $h^{-1}$.

According to the invention, the $C_1$-$C_4$-aliphatics are converted in step I to aromatics with release of $H_2$. Product stream P therefore comprises at least one aromatic hydrocarbon selected from the group of benzene, toluene, ethylbenzene, styrene, xylene and naphthalene. It more preferably comprises benzene and toluene. In addition, the product stream comprises unconverted $C_1$-$C_4$-aliphatics, hydrogen formed, and the inert gases present in reactant stream E, such as $N_2$, He, Ne, Ar, substances added to reactant stream E, such as $H_2$, and impurities already present in E.

According to the invention, the catalyst used for the DHAM in step I is regularly regenerated with the hydrogen present in gas stream H in step III. This converts at least a portion of the deposited coke to methane. The regeneration according to stage III in reaction zone 2 is performed at temperatures of 600° C. to 1000° C. and more preferably of 700° C. to 900° C., and pressures of 1 bar to 30 bar, preferably of 1 bar to 15 bar and more preferably of 1 to 10 bar. This forms a methane-containing gas stream M which, as well as the methane formed, comprises further compounds formed in the regeneration, unconverted hydrocarbon and substances already present in mixture H.

In a preferred embodiment of the present invention, the temperature of the catalyst on entry into reaction zone 1 is above the temperature on entry into reaction zone 2. The entrance temperature into reaction zone 1 is preferably at least 50° C., preferably at least 75° C., and more preferably at least 100° C. above the entrance temperature into reaction zone 2.

According to the invention, at least a portion of the methane formed in the regeneration is fed to reaction zone 1. More preferably at least 50%, more preferably at least 80%, most preferably at least 90%, of gas stream M, and especially the entire gas stream M, is fed from reaction zone 2 to reaction zone 1. In a preferred embodiment of the invention, the amount of hydrogen fed to reaction zone 2 and the geometric dimensions of reaction zone 2 are matched to the catalyst to be regenerated such that gas stream M on entry into reaction zone 1 comprises at most 10% by volume of hydrogen, preferably at most 5% by volume of hydrogen and very particularly no longer comprises any hydrogen, which means that the hydrogen supplied has been consumed very substantially and preferably completely in the regeneration in step III. This has an unfavorable effect on the reaction equilibrium of the DHAM in reaction zone 1.

According to the invention, the catalyst is transferred in step II from reaction zone 1 to reaction zone 2, and at least a portion of gas stream M is transferred in step III directly from reaction zone 2 into reaction zone 1, i.e. without diversion, in the region in which the two reaction zones spatially adjoin. According to the invention, the mean flow direction of gas stream M is counter to the mean flow direction of the particulate catalyst.

In a preferred embodiment of the present invention, reaction zone 2 is arranged below reaction zone 1. In this case, reactant stream E is preferably fed to the lower part of reaction zone 1, more preferably to the lower third and most preferably to the lowermost quarter of reaction zone 1. The product stream P formed in the DHAM is discharged from reaction zone 1 in the upper part of reaction zone 1, preferably from the upper third and more preferably from the uppermost quarter of reaction zone 1.

The hydrogen-comprising gas stream H is fed in step III, in the case of arrangement of reaction zone 2 below reaction zone 1, to the lower part, preferably to the lower third and more preferably to the lowermost quarter of reaction zone 2.

The catalyst optionally heated outside reaction zone 2 is, in the case of arrangement of reaction zone 2 below reaction zone 1, recycled in step V, preferably into the upper part of reaction zone 1, preferably into the upper third and more preferably the uppermost quarter of reaction zone 1; the catalyst is most preferably recycled into reaction zone 1 from above.

In the dehydroaromatization of $C_1$-$C_4$-aliphatics in step I, and also in the regeneration of the catalyst deactivated by coke deposits with hydrogen in step III, the catalysts may be present in the form of a fluidized bed or moving bed in the corresponding reactor types suitable therefor.

Preferably, according to the present invention, the catalyst is present in the form of a fluidized bed in reaction zone 1, in reaction zone 2 or in both reaction zones. Preferably, according to the present invention, the operating parameters, reactor configuration and reactor dimensions are selected such that essentially no gas backmixing occurs between reaction zone 1 and reaction zone 2, in order if possible to prevent introduction of $C_1$-$C_4$-aliphatics from reaction zone 1. Since the reductive regeneration of the catalyst forms methane, an introduction of $C_1$-$C_4$-aliphatics, especially of methane, has an adverse effect on the reaction equilibrium of the regeneration.

More preferably, reaction zone 2 is operated as a fluidized bed, in which case essentially no internal mixing occurs. Internal mixing should be substantially suppressed in order to prevent or at least to reduce backmixing of the methane-comprising gas stream M into reaction zone 2 and thus to ensure a very pure hydrogen atmosphere in reaction zone 2. More particularly, a very low-methane gas phase in reaction zone 2 leads to a higher conversion of methane in reaction zone 1, as shown in the example. In addition, the reduction in internal mixing achieves a more homogeneous residence time profile of the catalyst particles for regeneration.

The conditions for the operation of the catalyst bed with minimum internal mixing are known to those skilled in the art. Indications for the selection of the parameters/operating conditions can be found, for example, in D. Kumii, O. Levenspiel "Fluidization Engineering Second Edition, Boston, chapter 9, pages 211 to 215 and chapter 10, pages 237 to 243.

A further means of reducing internal mixing in the reaction zone is the incorporation or the arrangement of devices which hinder internal mixing. These devices may, for example, be perforated sheets, structured packings, guide plates and further internals known to those skilled in the art. In a preferred embodiment, at least one such device is arranged in reaction zone 2. The extent of the internal mixing can be determined, for example, by the vertical dispersion coefficients.

Preferably less than 10 mol % of $C_1$-$C_4$-aliphatic, especially methane, based on stream H, is introduced from reaction zone 1 into reaction zone 2 by backmixing.

The transition region between reaction zones 1 and 2 is preferably at most 25%, more preferably at most 10% and most preferably at most 5% of the length of reaction zone 1. Length of reaction zone 1 means the extent of the reactor in the flow direction of stream E.

Preferably in accordance with the invention, reaction zone 1 is separated from reaction zone 2 by at least one device which is pervious to the reaction gases and the catalyst particles and is arranged in the transition region between reaction zones 1 and 2. These devices may be perforated sheets, guide plates, structured packings and further internals known to the person skilled in the art for this purpose, as described, for example, in Handbook of Fluidization and Fluid-Particle Systems, New York, 2003, Editor W. Yang, chapter 7, pages 134 to 195. These devices can influence the backmixing of the catalyst particles and of the reaction gases between these two zones. Reaction gases in the context of the invention refer to the entirety of the gas streams involved in reaction zones 1 and 2, i.e. gas streams E, H, P and M.

Preferably in accordance with the invention, reaction zone 1 is operated as a bubble-forming or turbulent fluidized bed, typically at superficial velocities of 10 to 80 cm/s.

Preferably, according to the invention, the catalyst on the one hand and the different gas streams E, H and M on the other hand are conducted in countercurrent. When reaction zone 2 is arranged below reaction zone 1 in the above-described preferred embodiment, this means that the catalyst on average flows from the top downward and gas streams E, H, M and P have a mean flow direction from the bottom upward.

Three reactor forms particularly suitable for the performance of the process according to the invention are shown in FIG. 1. Reactor form (a) is cylindrical in the region of reaction zone 1 and, in the region of reaction zone 2 arranged below reaction zone 1, is likewise cylindrical with the same diameter as in the region for reaction zone 1. The reactor with reactor form (b) is cylindrical in the region of reaction zone 1 and, in the region for reaction zone 2, is likewise cylindrical but with a smaller diameter than in the region for reaction zone 1 and has a conically shaped transition part. Reactor form (c) likewise has a cylindrical region for reaction zone 1 and is completely conically shaped in the region of reaction zone 2 arranged below it.

According to the invention, more than one reaction zone 1 and more than one reaction zone 2 may be present; it is merely necessary in each case that at least one reaction zone 1 and at least one reaction zone 2 which spatially adjoin one another are present.

According to the invention, the catalyst can be used undiluted or mixed with inert material. The inert material used may be any material which behaves inertly, i.e. does not react, under the reaction conditions which exist in the reaction zones. Suitable inert materials are particularly the undoped support used for the catalyst, but also inert zeolites, aluminum oxide, silicon dioxide, etc. The particle size of the inert material is in the region of the size of the catalyst particles. The catalyst is preferably used mixed with inert material. According to the invention, the inert material serves as an inexpensive heat transfer in order to introduce thermal energy into reaction zone 1. It is particularly advantageous to mix the catalyst with less expensive inert material when reaction zone 2 is arranged below reaction zone 1, since the mixing with inert material increases the height of the reactor or of the reactor bed. This leads to a greater pressure drop along the fluidized bed. The highest pressure is established at the lower end of the reactor bed, i.e. in reaction zone 2. A higher pressure has a positive effect in the regeneration.

For regeneration of the catalyst deactivated by coke deposits from step I, it is, according to the invention, regularly regenerated in reaction zone 2 with hydrogen. To this end, the catalyst from reaction zone 1 is transferred into reaction zone 2 and regenerated there with the aid of the hydrogen-comprising gas stream H. The regenerated catalyst is then recycled back into reaction zone 1.

The heat which arises in the course of regeneration of the catalyst in step III in reaction zone 2 is fed to reaction zone 1 in order to at least partly contribute to coverage of the energy required for the DHAM in step I. The heat is supplied by transferring at least some of the regenerated catalyst from reaction zone 2 into reaction zone 1. The regenerated catalyst serves as a heat carrier. At least a further portion of the heat which arises in the course of regeneration of the catalyst in step III in reaction zone 2 is fed directly to reaction zone 1 through gas stream M.

In a further preferred embodiment of the present invention, some of the energy required in reaction zone 1 in step I of the present process is supplied indirectly, for example by means of a heat exchanger bundle in reaction zone 1.

In a further preferred embodiment of the present invention, some of the energy required in reaction zone 1 in step I of the present process is supplied by, after step IV and before step V, heating at least a portion of the discharged catalyst with any inert material present to a temperature above the temperature in reaction zone 1. According to the invention, the process then comprises the steps of I. feeding reactant stream E into a reaction zone 1, converting reactant stream E under nonoxidative conditions in the presence of a particulate catalyst to a product stream P comprising aromatic hydrocarbons and discharging product stream P from reaction zone 1, II. transferring the catalyst with reduced activity as a result of deposited coke into a reaction zone 2, III. at least partly regenerating the catalyst with supply of a hydrogen-comprising gas stream H in a reaction zone 2, at least some of the coke deposited being converted to methane to form a methane-comprising gas stream M which is fed at least partly to reaction zone 1, IVa. discharging the catalyst from reaction zone 2, IVb. heating at least a portion of the catalyst and V. recycling at least a portion of the heated catalyst into reaction zone 1, reaction zone 1 and reaction zone 2 being arranged spatially adjacent to one another in the same reactor.

At least some, preferably all, of the catalyst discharged in step IVa, optionally with the inert material added, is heated outside reaction zones 1 and 2 to a temperature which is at least 50° C., preferably at least 75° C. and more preferably at least 100° C. above the temperature in reaction zone 1. At least some, preferably all, of the heated catalyst is recycled into reaction zone 1. The discharged catalyst can be heated directly or indirectly. The discharged catalyst is preferably heated directly by, for example, conducting combustion gases through the catalyst. In a preferred embodiment of the process according to the invention, an inert gas is heated, for example with combustion gases, which then heats the catalyst in direct contact. The heating of the catalyst and optionally of the inert material is preferably performed in a so-called riser known to those skilled in the art.

In spite of the regular regeneration of the catalyst on each pass of the catalyst through reaction zones 1 and 2, it may be advisable from time to time to regenerate the catalyst outside reaction zone 2. To this end, the catalyst, after being discharged from reaction zone 2 in step V and before being recycled into reaction zone 1, is reductively and/or oxidatively regenerated and optionally also activated. This additional regeneration step is performed at most after every second pass, preferably at most after every tenth and more preferably at most after every 50th pass of the catalyst. Reductive regeneration means that the regeneration takes place in reductive atmosphere, preferably in hydrogen atmosphere. The oxidative regeneration is undertaken under oxidizing conditions, i.e. in the presence of oxidizing agents, especially in the presence of an oxygen-comprising gas such as air. In the oxidative regeneration, the carbon deposited on the catalyst is converted to CO and $CO_2$. The oxidative regeneration is typically followed by a reactivation step as described above for the activation of the freshly prepared catalyst.

EXAMPLES

Influence of the Methane Content in the Hydrogen Used for Catalyst Regeneration

Example 1

In a fixed bed, two reaction cycles in each case of the aromatization of methane were conducted with a duration of 10 h at 700° C. and ambient pressure. Between the two reaction cycles, the catalyst was regenerated at 750° C. bar (abs) for 5 h.

a) Regeneration with pure hydrogen b) Regeneration with a mixture of 90% by volume of hydrogen and 10% by volume of methane The methane conversions (based on the methane used in the reaction cycles) are lower in the case of regeneration with the gas stream comprising methane and hydrogen, as shown in Table 1.

TABLE 1

|  | Example 1a) | Example 1b) |
| --- | --- | --- |
| Regeneration gas | 100% $H_2$ | 10% $CH_4$/90% $H_2$ |
| Methane conversion in 1st cycle | 9% | 9% |
| Methane conversion in 2nd cycle | 9% | 7% |

Backmixing of the methane in the direction of the regeneration zone (reaction zone) will have an adverse effect on the efficiency of the regeneration.

The invention claimed is:

1. A process, comprising:
feeding a reactant stream E comprising a $C_1$-$C_4$ aliphatic into a reaction zone 1,
converting reactant stream E under nonoxidative conditions in the presence of a particulate catalyst into a product stream P, comprising an aromatic hydrocarbon,
discharging product stream P from reaction zone 1,
transferring the catalyst into a reaction zone 2, the catalyst having reduced activity as a result of deposited coke,
at least partly regenerating the catalyst with a supply of a hydrogen-comprising gas stream H in a reaction zone 2, thereby converting at least some of the coke deposited into methane to form a methane-comprising gas stream M,
feeding the gas stream M at least partly to reaction zone 1,
discharging the catalyst from reaction zone 2, to obtain a discharged catalyst, and
recycling at least a portion of the discharged catalyst into reaction zone 1,
wherein reaction zone 1 and reaction zone 2 are adjacent to one another in a reactor and
wherein essentially no gas backmixing occurs between reaction zone 1 and reaction zone 2.

2. The process of claim 1, further comprising:
heating at least a portion of the discharged catalyst after discharging and before recycling.

3. The process of claim 1, wherein a device that is pervious to the catalyst and to reaction gases is between reaction zone 1 and reaction zone 2.

4. The process of claim 1, wherein reaction zone 2 comprises a fluidized bed with essentially no internal mixing.

5. The process of claim 1, wherein reaction zone 2 comprises a device that hinders internal mixing of catalyst particles in the fluidized bed.

6. The process of claim 1, wherein reaction zone 1 comprises a fluidized bed with internal mixing.

7. The process of claim 1, wherein gas stream M on entry into reaction zone 1 comprises at most 10% by volume of hydrogen.

8. The process of claim 1, wherein reaction zone 2 is below reaction zone 1.

9. The process of claim 8, wherein recycling at least a portion of the discharged catalyst into reaction zone 1 comprises supplying the discharged catalyst to an upper part of reaction zone 1.

10. The process of claim 8, wherein at least partly regenerating the catalyst with a supply of a hydrogen-comprising gas stream H comprises supplying gas stream H to a lower part of reaction zone 2.

11. The process of claim 8, wherein feeding reactant stream E into a reaction zone 1 comprises supplying the reactant stream E to a lower part of reaction zone 1.

12. The process of claim 1,
wherein the reactor is cylindrical in reaction zone 1, and
in a region of reaction zone 2 below reaction zone 1, the reactor is (a) cylindrical with a diameter equal to a diameter of reaction zone 1, (b) cylindrical with a diameter smaller than a diameter of reaction zone 1 and with a conically shaped transition part, or (c) completely conically shaped.

13. The process of claim 1, wherein converting reactant stream E is in the presence of the catalyst mixed with inert material.

14. The process of claim 1, further comprising:
oxidatively, reductively, or both oxidatively and reductively regenerating the catalyst, after discharging from reaction zone 2 and before the recycling into reaction zone 1, and
optionally reactivating the catalyst, at most after every second pass of the catalyst through the reaction zones 1 and 2.

15. The process of claim 1, wherein, during converting reactant stream E to product stream P, a content of oxidizing agents in a reaction mixture is below 1% by weight.

16. The process of claim 1, wherein gas stream H comprises below 5% by weight of oxidizing agents.

17. The process of claim 1, wherein a content of $C_1$-$C_4$-aliphatic in reactant stream E is at least 50 mol %.

18. The process of claim 17, wherein a content of alkanes having from 1 to 4 carbon atoms in reactant stream E is at least 60 mol %.

19. The process of claim 1, wherein reactant stream E comprises hydrogen in a content of from 0.1 to 10% by volume.

* * * * *